United States Patent [19]

Grey et al.

[11] Patent Number: 4,590,313

[45] Date of Patent: May 20, 1986

[54] METHOD FOR PRODUCING PRIMARY ALCOHOLS BY CATALYTIC HYDROGENATION OF TERMINAL EPOXIDES

[75] Inventors: Roger A. Grey, West Chester; John F. White, Villanova; Eva M. Beals, Washington Crossing, all of Pa.

[73] Assignee: Atlantic Richfield Company, Los Angeles, Calif.

[21] Appl. No.: 384,318

[22] Filed: Jun. 2, 1982

[51] Int. Cl.[4] .................... C07C 29/132; C07C 31/10; C07C 31/12
[52] U.S. Cl. ..................................... 568/907; 568/678
[58] Field of Search .......................... 568/907

[56] References Cited

U.S. PATENT DOCUMENTS 1,787,205 12/1930 Loehr .................................. 568/907
3,975,449 8/1976 Suzuki ............................. 260/635 E

FOREIGN PATENT DOCUMENTS 838189 3/1970 Canada ................................. 568/907
1139477 11/1962 Fed. Rep. of Germany .
48-31083 9/1973 Japan .
496264 11/1938 United Kingdom ................ 568/907
970790 9/1964 United Kingdom ................ 568/907

OTHER PUBLICATIONS

Chernyshkova, F. A., et al., *Neftekhimiya*, 1974, 14(20), pp. 188–192 (translation only).
Senechal & Cornet, *Bull. Soc. Chim.*, 11, 773 (1971) (translation only).

*Primary Examiner*—J. E. Evans
*Attorney, Agent, or Firm*—Craig E. Larson

[57] ABSTRACT

A process for producing primary alcohols from terminal epoxides having a mono-substituted epoxy ring and having from 3 to 6 carbon atoms per molecule which process comprises contacting the epoxide and hydrogen gas with Raney cobalt catalyst under vapor phase conditions in a hydrogenation zone.

2 Claims, No Drawings

METHOD FOR PRODUCING PRIMARY ALCOHOLS BY CATALYTIC HYDROGENATION OF TERMINAL EPOXIDES

BACKGROUND OF THE INVENTION

1. FIELD OF THE INVENTION

The present invention relates to catalytic hydrogenation of terminal epoxides. The present invention more particularly relates to an improved process for producing primary alcohols at high conversions and selectivities by catalytic hydrogenation of lower, terminal, epoxides which contain a mono-substituted epoxy ring.

2. DESCRIPTION OF THE PRIOR ART

Lower primary alcohols and diols are useful as solvents, particularly in the coatings industry. Other useful materials are derived from these materials, for example the acetates. These materials are also useful as intermediates for producing plasticizers such as dibutylphthalate.

Known methods for synthesizing primary alcohols are: (1) by way of organo-aluminum compounds, (2) by hydrogenation of methyl esters or fatty acids, and (3) by catalytic hydrogenation of aldehydes produced by the Oxo process.

Hydrogenation of terminal aliphatic epoxides to corresponding primary alcohols is also known and is known to be catalyzed by metals such as nickel, cobalt, iron, and copper. The primary alcohols produced, however, contain by-product secondary alcohols, and catalyst systems capable of high conversion with high selectivity to the primary alcohol product have been sought. Japanese Patent Publication No. 73-31083 discloses the production of primary straight chain aliphatic alcohols from 1,2-epoxy straight chain alkanes having at least 3 carbon atoms by liquid phase hydrogenation in the presence of nickel boride, cobalt boride, iron boride, or copper boride at a temperature of 80°–200° C. and a hydrogenation pressure of 20–300 atmospheres.

Senechal and Cornet, "Hydrogenation and Deuteration of 1,2-Epoxybutane and 2,3-Epoxybutane on Metal Catalysts," *Bull. Soc. Chim. France*, No. 3, pp. 773–783 (1971) reports a study of vapor phase hydrogenation of 1,2-epoxybutane to butanols over Cu,Ni,Pt,Pd,Rh,Ag, and Au catalysts. Ni and Cu catalysts were found to favor cleavage between oxygen and the substituted carbon of the epoxybutane. Both catalysts, however, exhibited a strong tendency to form saturated hydrocarbons. Saturated hydrocarbons represented 22% and 42% of the reaction products over Ni and Cu, respectively, at 140° C. The results reported in the article also indicate significant epoxide isomerization occurred under the conditions employed. The article further notes that catalytic cleavage of epoxy rings is generally studied with reagents in the liquid phase, although, as noted, the studies reported in this article employed reagents in the gaseous phase.

Chernyshkova, F. A., et al., *Neftekhimiya*, 14 (20), pp. 188–92 (1974) reports a study of the hydrogenation of 1,2-epoxyhexane over zeolite catalysts. The article notes the problem of hydrocarbon formation during hydrogenation of terminal epoxides to alcohols. Zeolites, both with and without hydrogenating metals (i.e., Ni,Pd,Cu,Mo,Fe), were examined. When 1,2-epoxyhexane was hydrogenated over Ni/zeolite Y, the content of primary alcohol in the total alcohols formed was 96%, although the overall selectivity of the epoxide to the primary alcohol was only about 80%.

German Patent No. 1,139,477 discloses a method for producing primary alcohols which contain virtually no secondary alcohols (but do contain paraffin reduction products) by catalytic hydrogenation of terminal, straight chain epoxides having from 7 to 20 carbon atoms per molecule. Group VIII metals (e.g., Co,Fe,Ni) are generally suggested by the patent to be effective hydrogenation catalysts. The hydrogenation catalysts may be prepared as finely-divided metals deposited on carriers or as finely-divided Raney metals. The best selectivities reported in the patent were obtained by adding small amounts of Th,Mg or alkali metals to the catalyst formulation. The process of the German patent may be operated continuously, either under conditions such that the epoxide reactant is in a gaseous state or under conditions such that the epoxide is in a liquid state. In other words, the physical state of materials present in the reaction zone is indicated to have no particular effect on the results obtained. The examples show that hydrogenation of 1,2-epoxyoctane over CoThMg/kieselguhr yielded 86% primary alcohol (the balance of the product being octane). Raney Ni; Raney Co;Co/C;Co/kieselguhr; and and NiThMg/kieselguhr were less selective for primary alcohols (for the $C_7+$ epoxy compounds studied) than CoThMg/kieselguhr.

U.S. Pat. No. 3,975,449 discloses a process for producing a primary diol and/or triol from a branched chain epoxide wherein the epoxide is hydrogenated in the presence of a solid catalyst comprising Ni or Co at a temperature of 20°–200° C. and a pressure sufficient to maintain the epoxide feed and the diol/triol products in the liquid phase. Suitable epoxide starting materials are defined by the following structural formula:

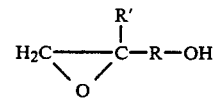

wherein R is an alkylene diradical of 1 to 5 C atoms and R' is a hydroxy alkyl or an alkyl having from 1 to 5 C atoms. Preferred catalyst are Raney Ni, supported Ni, and Raney Co, with Raney Ni being particularly preferred. Hydrogen pressures in the process are within the range from 100–10,000 psig, preferably from 500–5,000 psig.

The primary object of the present invention is an improved process for the hydrogenation of hydrocarbon compounds containing a terminal epoxy ring, and having from 3 to 6 C atoms/molecule, to produce high yields of primary alcohol products. Other objects will be apparent from the following description of this invention.

SUMMARY OF THE INVENTION

It has now been found that primary alcohols can be selectively produced in high yields by vapor phase hydrogenation of terminal epoxides, comprising a mono-substituted epoxy ring and having from 3 to 6 C atoms/molecule, over Raney cobalt catalysts. Both the use of Raney Co catalyst and vapor phase operation of the reaction zone are critical to the results attained by the process of this invention.

Hydrogenation of terminal epoxides over Raney Co is known (see Description of the Prior Art, supra). German Patent No. 1,139,477 shows hydrogenation of $C_8$–$C_{16}$ straight-chain, aliphatic terminal epoxides; the product fraction, obtained by hydrogenation of 1,2-octene oxide over Raney Co in an autoclave reactor, contained 71 wt. % of 1-octanol. U.S. Pat. No. 3,975,449 teaches liquid-phase hydrogenation of disubstituted, terminal epoxy rings. Examples 4 and 5 of the U.S. patent shows liquid-phase hydrogenation of 2,3-epoxy-2-methyl propanol over Raney Co; the product fractions obtained over Raney Co contained from about 40–60 wt. % of the corresponding primary diol.

The German patent teaches that the epoxide reactant may be present in the reaction zone in liquid or gaseous states, and is silent with respect to the physical state of the alcohol product. The U.S. patent teaches a liquid-phase reaction zone.

During preliminary, batch testing in a Parr bomb reactor, the present inventors found that primary alcohol selectivities up to about 82 wt. % could be obtained by liquid-phase hydrogenation of lower, terminal epoxides, comprising a mon-substituted epoxy ring, over a Raney cobalt catalyst. Surprisingly, it was discovered that primary alcohol product selectivities were dramatically enhanced when reactor conditions were modified such that the epoxy reactants and alcohol products were present substantially as vapor in the reactor. Furthermore, it was discovered that this phase effect is unique to Raney Co hydrogenation catalysts—e.g., similar yield enhancement was not found when phase effects were examined over supported cobalt or nickel catalysts.

Previous studies indicated that primary alcohol selectivities obtained by hydrogenation of terminal epoxides over Raney Ni are better than those obtained over Raney Co. However, it has now been discovered that the primary alcohol selectivity of Raney Co is superior to that of Raney Ni if the hydrogenation over Raney Co is conducted in the vapor phase.

Accordingly, a principal improvement of the method of this invention is the capability of obtaining high selectivities (up to about 95 wt. %) of primary alcohol products by hydrogenation of lower, terminal epoxides over a Raney Co catalyst and by conducting the hydrogenation reaction in the vapor phase—i.e., both the epoxide reactants and alcohol products are present in the reaction zone in a gaseous state.

DETAILED DESCRIPTION OF THE INVENTION

"Terminal epoxides, comprising a mono-substituted epoxy ring and having from 3 to 6 C atoms/molecule" refers to compounds described by the following structural formulae:

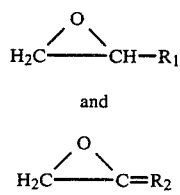

wherein R and $R_2$ are straight or branched chain, alkyl or alkenyl radicals having from 1 to 4 carbon atoms. Examples of suitable hydrogenation feedstocks for the process of this invention thus include propylene oxide; 1,2-butylene oxide; propadiene monoepoxide; terminal monoepoxides of 1,3- and 1,2-butadiene; 1,2-epoxy-3-methyl pentane; and 4,5-epoxy-3-methyl-2-pentene. Presently preferred feedstocks are terminal straight-chain epoxides, especially propylene oxide and 1,2-butylene oxide.

Hydrogenation products produced by the process of this invention are, predominantly, primary alcohols which have a structure corresponding to the epoxide reactant.

Raney cobalt is a well known hydrogenation catalyst. In general, this catalyst is prepared from an alloy made up of about 50% aluminum and about 50% cobalt. The finely powdered alloy is treated with an aqueous solution of sodium or potassium hydroxide until the alkali dissolves most of the aluminum in the alloy, leaving the cobalt in a finely divided, porous and highly active form. The cobalt is then washed several times with water and thereafter stored under water or other inert solvent until the catalyst is to be used. As is well known, this catalyst is relatively inexpensive on the basis of the amount of product produced, which offers an additional advantage to the process of the present invention. The term "Raney cobalt" referred to herein is intended to mean skeletal alloy catalysts which have been prepared by leaching aluminum from an alloy comprising principally cobalt and aluminum.

The Raney cobalt may be employed alone or in combination with a solid, essentially inert diluent. Suitable solid diluents include finely divided alkali metal halides, sand, and binders such as bentonite. Other suitable diluents will be apparent to one skilled in the art. Particle size of the solid diluents should be roughly equivalent to that of the Raney cobalt catalyst employed. The solid diluent should be essentially inert, i.e., the presence of the solid should not materially detract from the results obtained by the process. For reasons not presently understood, use of alkali metal halide diluents was found to enhance selectivities obtained by hydrogenation of lower terminal epoxides over Raney Co to form primary alcohols. Their use is accordingly a preferred embodiment of the present invention. An especially preferred diluent is NaCl.

Except for the requirement that the hydrogenation be carried out in the vapor phase—i.e., that the epoxide reactant and the formed products be maintained in a gaseous state in the catalytic reaction zone—the operating parameters of the process are within conventional ranges. Temperatures should be within the range from about 25° to 250° C., preferably from about 80° to 190° C. Pressures should be within the range from about 0.1 to 1000 atmospheres, preferably from about 20 to 100 atmospheres, still more preferably from 20 to 60 atmospheres.

Maintaining the epoxide reactant and its hydrogenation products in a gaseous state in the catalytic reaction zone is within the skill of the art. For example, vapor phase operation may be attained by raising reactor temperature, by lowering the reactor pressure or by lowering the partial pressure of the reactants and products in the reaction zone. Partial pressures may be reduced by increasing the amount of $H_2$ introduced into the reaction zone or by introducing a nonreactive gaseous or vapor-phase material to the hydrogenation zone. Suitable gaseous diluents include, for example, $N_2$ and argon. Other suitable diluents are exemplified by tert-butyl alcohol and hexane—i.e., organic materials which are nonreactive and will be vaporized under the operating conditions of the reaction zone. These latter diluents may be introduced along with the epoxide reactant to the hydrogenation zone.

The $H_2$: epoxide molar ratio is broadly within the range from about 1:1 to 120:1, although the ratio will preferably be within the range from about 10:1 to 20:1.

The process is operated continuously. The Raney cobalt catalyst may be maintained either as a fixed or fluidized bed. In the case of fixed bed operation, the flow of reactants may be either upflow or downflow, although the downflow mode is preferred.

Products leaving the reactor may be separated and recovered by means which are in the skill of the art.

Raney cobalt powder used in the following Examples was prepared from a 50% aqueous slurry of Raney Co obtained from a commercial source. The slurry was dried under vacuum at 150° C. for 3-5 hours. The dry powder thus obtained was reduced in a hydrogen stream by heating from 100° C. to 300° C. over a 6 hour period and then heating at 300° C. for 3 hours. The reduced Raney Co was stored in an argon filled dry box. It analyzed for 91.7% Co, 0.8% Fe, 3.4% Ni, and 3.7% Al.

EXAMPLE 1

A tubular reactor (7 cc volume) was charged with a mixture of 1 gram of the dried Raney Co and 6 grams of dry NaCl diluent. A preheated feed of 1,2-butylene oxide and hydrogen was introduced downflow through the catalyst bed. The molar ratio of $H_2$:BuO(i.e., 1,2-butylene oxide) was 20:1. Contact time in the reactor was 1 second (at standard temperature and pressure). Reaction temperature was controlled by circulating silicone oil around the reactor at a set temperature. Pressure was maintained at 500 psi. Reactor effluent, still heated at 500 psi, was split into two streams with 10% being analyzed for all components by on-line gas chromatography. Results obtained over the catalyst at various operating temperatures are described in Table I below. All results are shown on a molar basis. About 4 grams of BuO is reacted in each run.

TABLE I

| Run # | Temp. (°C.) | % Conversion | NBA/SBA$^c$ | Selectivity Total Alcohols | NBA |
|---|---|---|---|---|---|
| 1 | 124-183 | 84 | 26 | 98.5 | 94.9 |
| 2 | 146-173 | 86 | 27 | 98.5 | 95.0 |
| 3 | 140-157 | 91 | 22 | 97.7 | 93.4 |
| 4 | 138-143 | 93 | 24 | 99 | 95 |
| 5 | 122-123 | 47 | 21 | 97.7 | 93.2 |
| 6 | 142-145 | 91 | 25 | 97 | 93.3 |
| 7 | 145-150 | 84 | 22 | 96.5 | 92.3 |
| 8 | 150-162 | 96 | 23 | 96 | 92.0 |
| 9$^a$ | 156-160 | 96 | 24 | 83 | 80.0 |
| 10$^b$ | 144 | 93 | 23 | 98 | 93.9 |
| 11 | 165 | 98 | 37 | 94.5 | 92.0 |

$^a$This run demonstrates results obtained after a week of operation. The loss of NBA selectivity is accompanied by an increase in butane formation (20% of epoxide-free product). SBA selectivity remains about the same.
$^b$Catalyst regenerated with $H_2$ at 500 psi, 350-375° C., 3 hours.
$^c$"NBA" is normal-butanol. "SBA" is sec-butanol.

EXAMPLE 2

The procedure of Example 1 was repeated except that the feed was a mixture of BuO/heptane (10:1 weight ratio) and the contact time was 0.5 seconds at standard temperature and pressure. During the hydrogenation run, total pressure was maintained at 500 psi and the temperature at 160° C. Selectivities to normal butanol, secbutanol and butane were 93.7%, 4% and 2.3%, respectively, at 93% conversion.

COMPARATIVE EXAMPLE 1

This Example demonstrates liquid phase hydrogenation of 1,2-BuO over Raney cobalt powder. A 300 cc autoclave was charged with 2.0 grams Raney cobalt powder under an argon blanket, followed by an addition of 90 grams (110 ml.) of argon-saturated BuO. Hydrogen was added to give a total pressure of 800 psig and the pressure was maintained at that level throughout the reaction. After 16 hours, the analysis of the reaction mixture showed that normal butanol, sec-butanol, butane and hydroxy ether had been produced at selectivities of 82%, 6%, 9%, and 3%, respectively, and at a conversion of 83%. Hydroxy ethers result from the reaction of product butanols and the starting epoxide (e.g., 2-hydroxy-di-n-butyl ether).

EXAMPLES 3-6

Three Raney cobalt catalysts were evaluated for propylene oxide (referred to hereafter as "PO") hydrogenation using the same procedure outlined in Example 1 except that the feed was PO/hexane (10:1 weight ratio). The RaCo/NaCl catalyst (Examples 3-4) was prepared as in Example 1. The RaCo/sand catalyst (Example 5) differs only in the substitution of sand for NaCl. The RaCo/bentonite catalyst (Example 6) was prepared by mixing RaCo powder with bentonite as a binder to form granules. The ratio of RaCo:bentonite was 3:1 by weight. The results are shown in Table II below.

TABLE II

| Example | Temp. (°C.) | Press. (psi.) | Conversion (%) | NPA$^a$ | IPA$^b$ | P$^c$ | HE$^d$ |
|---|---|---|---|---|---|---|---|
| 3 | 170 | 800 | 99 | 93.3 | 4.1 | 2.4 | 0.1 |
| 4 | 194 | 500 | 96 | 89.8 | 4.5 | 5.4 | 0.3 |
| 5 | 160 | 500 | 89 | 89.7 | 8.0 | 2.2 | 0.1 |
| 6 | 122 | 500 | 99 | 90.1 | 4.8 | 6.8 | 0.6 |

$^a$Normal propanol
$^b$Isopropyl alcohol
$^c$Propane
$^d$Hydroxy ethers (e.g., 2-hydroxy-di-n-propyl ether resulting from the reaction of n-propanol and propylene oxide).

Of all the Raney cobalt catalysts studied, the best results were obtained using Raney cobalt powder physically mixed with NaCl (1:6 weight ratio). Since Raney cobalt mixed with sand and Raney cobalt granules prepared by bentonite gave slighty lower selectivities, it is possible that the NaCl diluent serves as a catalyst activator.

COMPARATIVE EXAMPLES 2-4

Following the procedure of Examples 3-6, PO hydrogenation over a number of cobalt catalysts other than Raney cobalt was examined. Table III below summarizes the results obtained for the best of these catalysts. The catalyst of comparative Example 2 is 35% Co supported on a refractory oxide carrier. The catalyst, identified as G-62, was obtained from United Catalysts, Inc. in the form of 3/16 inch pellets having a surface area of about 41 m$^2$/g. The catalyst of Comparative Example 3 is Harshaw Co-01-64 T, a reduced and stabilized catalyst containing 25% Co on a silica-alumina support (3/16 inch pellets, 60 m$^2$/g surface area). The catalyst of Comparative Example 4 is UCI catalyst G-61, a hydrogenation catalyst containing 67% Co on a kieselguhr support (3/16 inch pellets, 97 m$^2$/g surface area). See the footnotes to Table II, supra, for an explanation of the abbreviations appearing in Table III.

TABLE III

| Comparative Example | Temp. (°C.) | Press. (psi) | Convers. (%) | Selectivities (%) | | | |
|---|---|---|---|---|---|---|---|
| | | | | NPA | IPA | P | HE |
| 2 | 120 | 500 | 90 | 85 | 5 | 8.4 | 1.6 |
| 3 | 140 | 500 | 99 | 79 | 5 | 15.5 | 0.4 |
| 4 | 97 | 500 | 94 | 91.5 | 2.2 | 4.0 | 2.1 |

Note that the catalyst of Comparative Example 4 had a very high cobalt loading on the support (67%). As shown in Table III, this catalyst was initially very active, giving essentially total conversion and 90% normal propanol selectivity at 120° C. However, after 1 day's operation using this catalyst, conversion dropped to 72% and normal propanol selectivity leveled off at 89%. Hydroxyether make was also relatively high for this catalyst (as much as 5%).

What is claimed is:

1. A method for hydrogenating terminal epoxides, comprising a mono-substituted epoxy ring and having from 3 to 6 carbon atoms per molecule, to form the corresponding primary alcohol, which method comprises contacting the epoxide with hydrogen gas and a solid catalyst comprising Raney cobalt and a solid, substantially inert diluent comprising an alkaline metal halide, the weight ratio of Raney cobalt to said diluent being within the range of about 1:1 to 1:100, at a temperature between 25° C. and 250° and at a pressure sufficient to maintain the epoxide reactant and product alcohol in the vapor phase.

2. The method of claim 1 wherein the solid diluent is NaCl.

* * * * *